United States Patent [19]

Efner

[11] Patent Number: 4,954,654
[45] Date of Patent: Sep. 4, 1990

[54] PROCESS FOR THE PREPARATION OF SECONDARY AND TERTIARY AMINES

[75] Inventor: Howard F. Efner, Bartlesville, Okla.

[73] Assignee: Phillips Petroleum Company, Bartlesville, Okla.

[21] Appl. No.: 237,380

[22] Filed: Aug. 29, 1988

[51] Int. Cl.$^5$ .......................................... C07C 209/26
[52] U.S. Cl. ..................................... 564/446; 564/472
[58] Field of Search .................... 564/446, 472, 473

[56] References Cited

U.S. PATENT DOCUMENTS

| | | | |
|---|---|---|---|
| 3,520,933 | 7/1970 | Adam et al. | 260/585 |
| 4,138,437 | 2/1979 | Strauss et al. | 260/583 |
| 4,234,727 | 11/1980 | Toussaint et al. | 655/178 |
| 4,505,860 | 3/1985 | Klein et al. | 260/453 |
| 4,521,624 | 6/1985 | Jackisch | 564/446 |

FOREIGN PATENT DOCUMENTS

| | | | |
|---|---|---|---|
| 60-104040 | 6/1985 | Japan | 564/472 |
| 679014 | 9/1952 | United Kingdom | 564/446 |

Primary Examiner—James H. Reamer
Attorney, Agent, or Firm—Laney, Dougherty, Hessin & Beavers

[57] ABSTRACT

A process for the preparation of secondary and tertiary amines such as dimethylcyclohexylamine, comprising reacting an amine of the formula

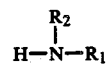

wherein $R_1$ is an organic group and $R_2$ is an organic group or hydrogen atom, with a ketone such as cyclohexanone in the liquid phase in the presence of an unsupported metallic copper catalyst under hydrogenating conditions. The process further includes providing an acid such as acetic acid as a condensation promoter, permitting the metallic copper catalyst to separate out by gravitation over a period of time, removing post-reaction material from contact with the catalyst, separating the post-reaction material into fractions, as by distillation, and recycling unreacted starting material for further reaction.

12 Claims, No Drawings

PROCESS FOR THE PREPARATION OF SECONDARY AND TERTIARY AMINES

BACKGROUND OF THE INVENTION

1. Field of the Invention

The present invention relates to a process for the preparation of secondary and tertiary amines, and more particularly, but not by way of limitation, to a process for the preparation of dimethylcyclohexylamine from cyclohexanone and dimethylamine.

2. Description of the Prior Art

Secondary and tertiary amines have a wide variety of industrial uses, i.e., as reactive intermediates, acid neutralizers in syntheses, polymerization catalysts in the preparation of polyurethanes, in bactericides, in pharmaceuticals, in insecticides, and as corrosion inhibitors. Accordingly, a number of processes have been proposed for the preparation of secondary and tertiary amines from less substituted amines, and these processes employ various catalysts under a variety of conditions.

One group of such processes has proposed employing catalysts from the transition metals of group 8 of the periodic table, and in particular, nickel in the form of Raney nickel has been employed as a hydrogenation catalyst. Raney nickel and other catalysts from this group, however, tend to lead to the production of by-products. For instance, in the preparation of dimethylcyclohexylamine from cyclohexanone and dimethylamine, it has been found that the use of Raney nickel results in yields of from 10 to 20 percent cyclohexanol through the reduction of unreacted cyclohexanone. Because of the closeness of the boiling points of the dimethylcyclohexylamine and cyclohexanol products, separation by distillation is made impracticable. In addition, it has been found that Raney nickel tends to deactivate on standing in the presence of the product mixture in the dimethylcyclohexylamine process. Raney nickel is also highly pyrophoric.

A second group of processes has suggested employing oxides possessing dehydrating properties, for example, aluminum oxide or silicon dioxide, usually at high temperatures and high pressures. As a result of the conditions under which this group of processes is typically conducted, energy and equipment demands are relatively high. In addition, the high temperatures employed tend to lead to a greater variety of products and undesired reactions.

A third group of processes known to the art has suggested some sort of copper-based catalyst For example, U.S. Pat. No. 4,234,727 to Toussaint et al. discloses the use of a supported copper catalyst for the gas phase production, at from 100° C. to 250° C. and atmospheric pressure, of dimethylcyclohexylamine from dimethylamine and cyclohexanone.

U.S. Pat. No. 3,520,933 to Adam et al. discloses the use of a supported copper-containing catalyst which further contains 0.1 percent to 15 percent of a pyroacid or polyacid in the liquid phase reaction of an alcohol or carbonyl compound with ammonia, a primary or a secondary amine. The total pressure is disclosed as ranging from 20 to 400 atmospheres, and the temperature from 80° C. to 230° C.

U.S. Pat. No. 4,505,860 to Klein et al. discloses the use of Raney copper to catalyze the reductive amination of the product of the reaction of certain cyclic keto-butyraldehydes and ammonia, thereby producing a primary diamine. The diamine is then reacted with phosgene to produce a cyclic diisocyanate cross-linking agent.

U.S. Pat. No. 4,138,437 to Strauss et al. discloses a process for the formation of tertiary amines wherein liquid phase alcohol or aldehyde reagents having 7 to 23 carbon atoms are reacted with a gaseous mixture of hydrogen and a lower primary or secondary alkylamine having at least one methyl group in the presence of a copper-chromium oxide catalyst. The addition of metal oxides of the first and second groups of the periodic system such as potassium, magnesium or barium is also suggested. The temperature is disclosed as being within the range of 160° C. to 230° C., with the partial pressure of hydrogen being within the range of 1–5 atmospheres. The catalyst is disclosed as being suitably supported or unsupported by a carrier.

As shown by these disclosures, it has been generally known within the third group of processes described above to use a supported copper-containing catalyst in combination with a condensation promoter such as an acid or in combination with an activity-boosting metal oxide in the synthesis of secondary and tertiary amines from carbonyl compounds. One problem encountered with such supported catalysts in batch reactions is that such catalysts frequently will be reduced in particle size during the reaction to such an extent that gravitational settling of the catalyst at the end of the reaction is inhibited. Separation of the catalyst from the product mixture is thereby made more difficult, time-consuming, and expensive. A problem has also been noted with the addition of alkaline reagents such as the oxides just mentioned, in that such additives can cause the catalyst composition to agglomerate so that the activity of the catalyst composition rapidly declines in continuous operation.

As shown by the above-mentioned disclosures, there is a need for a catalytic process which does not result in the significant production of unwanted by-products, which can be performed at lower temperatures to lower energy consumption and reduce the production of by-products, and in which catalytic activity is not significantly diminished on shutting down a reactor. Further, there is a need for such a process that permits the efficient and effective separation of the products and residual reactants from each other and from the catalyst.

SUMMARY OF THE INVENTION

The present invention attains the objects and fulfills the needs mentioned above, and overcomes the above-noted and other shortcomings of the prior art, by providing a novel process for the preparation of secondary and tertiary amines by the reaction of an amine of the formula:

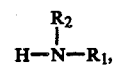

wherein $R_1$ is an organic group and $R_2$ is an organic group or hydrogen atom, with a ketone in the liquid phase in the presence of an unsupported metallic copper catalyst under hydrogenating conditions.

In accordance with the process of the present invention, dimethylcyclohexylamine is formed by the liquid-phase reaction of the cyclic ketone cyclohexanone and dimethylamine in the presence of a dispersed Raney copper catalyst and a pressure of hydrogen of at least 200 psig, at temperatures ranging from about 100° C. to about 120° C. An acid is provided as a condensation promoter. The condensation promoter in the synthesis of dimethylcyclohexylamine is acetic acid, and the acetic acid so provided is present in concentrations in the range of from about 1 weight percent to about 4 weight percent of the cyclohexanone added.

The process for preparation of secondary and tertiary amines generally, and dimethylcyclohexylamine in particular, includes permitting the metallic copper catalyst to separate out by gravitation over a period of time, removing post-reaction material from contact with the catalyst, and separating the post-reaction material into fractions, as by distillation. The process further includes the step of recycling unreacted starting material for further reaction.

In accordance with the above needs, it is an object of the present invention to enable the synthesis of secondary and tertiary amines with a minimum of unwanted by-products at a relatively low temperature and pressure, in which the catalytic activity of the process catalyst is not significantly diminished on shutting down a reactor.

Another object of the present invention is to provide a process for the production of secondary and tertiary amines which is simple and economical, particularly in terms of the separation of products and residual reactants from each other and from the catalyst.

A further object of the present invention is to provide such a process which produces the desired secondary and tertiary amines in high yields, and where the desired amine is dimethylcyclohexylamine, to provide a process wherein the reduction of cyclohexanone as a reactant to cyclohexanol is minimized so that distillative separation of the dimethylcyclohexylamine at an acceptable degree of purity is made practicable.

Other objects and advantages will become more fully apparent to a person of ordinary skill in the art with a consideration of the following description and appended claims.

DETAILED DESCRIPTION OF THE PREFERRED EMBODIMENTS

The present invention provides a novel and improved process for the preparation of secondary and tertiary amines generally, and of dimethylcyclohexylamine in particular. The process for the preparation of secondary and tertiary 15 amines comprises reacting an amine of the formula:

$$H-\underset{\underset{R_1}{|}}{N}-R_2,$$

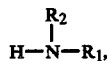

wherein $R_1$ is an organic group and $R_2$ is an organic group or hydrogen atom, with a ketone in the liquid phase in the presence of an unsupported metallic copper catalyst under hydrogenating conditions.

The process further comprises permitting the catalyst to separate out by gravitation, removing post-reaction material from contact with the catalyst, and separating the post-reaction material into fractions, as by distillation. Unreacted starting material may then be recycled for further reaction.

The process reaction is preferably carried out with an acid present as a condensation promoter and at temperatures in the range of from about 100° C. to 120° C., with 200 to 350 psig of hydrogen gas being provided for hydrogenation purposes, the 200 psig figure representing approximately the vapor pressure of the dimethylamine at the suggested temperatures. The reactant mixture preferably initially comprises from 1 to 1.25 mols of the amine per mol of the ketone.

It is thought that the reaction between the amine and the ketone, which is of the formula:

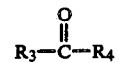

wherein $R_3$ and $R_4$ represent the same or different organic groups, but which ketone is preferably a cyclic ketone, produces an intermediate aminoalcohol, which is then hydrogenated to form the object secondary or tertiary amine:

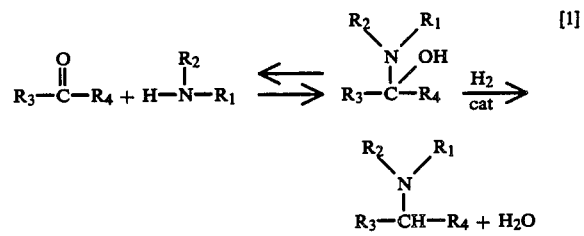

[1]

In the preferred embodiment, where the ketone reactant is a cyclic ketone generally, the amine reactant is most preferably present in the range of up to about 1.1 mols per mol of the cyclic ketone. The temperature of the reaction is in the range of from about 115° C. to 120° C., with the pressure of hydrogen provided for hydrogenation being about 250 psig. The acid of the aforementioned preferred embodiment is preferably acetic acid, and is present in a concentration in the range of from about 1 to about 4 weight percent by weight of ketone added. Stronger acids may be used, but may result in the formation of other products.

In the most preferred embodiment of the invention, the process comprises reacting cyclohexanone with the amine reactant dimethylamine to produce dimethylcyclohexylamine:

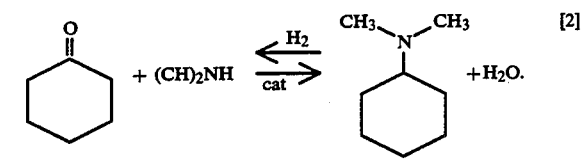

[2]

In the most preferred embodiment, a second competing reaction is also important, in that some degree of reduction of the cyclohexanone reactant is thought to take place also in the presence of the metallic copper hydrogenating catalyst and hydrogen gas:

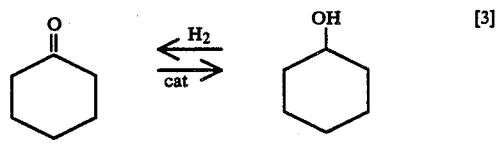

[3]

The primary difficulty occasioned by the production of cyclohexanol in the most preferred embodiment, as explained briefly earlier, lies in separating the cyclohexanol and dimethylcyclohexylamine, both of which have boiling points in the range of 160° C. to 161° C. Catalysts such as Raney nickel have displayed a greater propensity for promoting a production of cyclohexanol than the metallic copper catalyst of the most preferred embodiment, namely Raney copper, in that under the conditions specified Raney nickel produces from 10-20 percent cyclohexanol as compared to about 2 percent for the Raney copper catalyst. Other possible metallic copper catalysts for carrying out the process under the conditions specified for the preferred embodiment include copper powder and copper sponge.

It has been found that yield is maximized, and separation problems minimized, where the reaction between the cyclohexanone and dimethylamine is carried out in the liquid phase in the presence of the unsupported Raney copper catalyst under a pressure of hydrogen about 250 psig. The temperature is most preferably in the range of from about 115° C to 120° C., as temperatures in the 130° C. to 145° C. range have been found to increase the production of cyclohexanol. The reaction is mildly exothermic, so that temperature control to keep the temperature within the desired range is not difficult. In industrial applications, it is expected that a high temperature finish may be appropriately used, however, to drive the reaction to completion without substantially increasing the amount of cyclohexanol produced.

A condensation promoter in the form of acetic acid, which acid is most preferably present in the amount of 4 weight percent by weight of cyclohexanone added, is also provided to promote the formation of the intermediate and thus to shift the equilibrium of the reaction of the most preferred embodiment toward the production of the object dimethylcyclohexylamine. It should be noted that the equilibrium of this reaction lies to the reactant side, with only a relatively small portion of the cyclohexanone reacting to form the aminoalcohol intermediate on addition.

The effects of the acid concentration are seen in that a decrease in the concentration of the acetic acid to 1 weight percent in the most preferred embodiment described above was shown to cause the cyclohexanol production to rise to the upper limits of the 1 to 2 percent range. A slight excess is provided also of the dimethylamine reactant for the same equilibrium-shifting purposes, up to about 1.1 mols per mol of the cyclic ketone cyclohexanone.

It has been determined that the rate determining step of the reaction [1]is the formation of the intermediate aminoalcohol, whereas the hydrogenation of the stable intermediate proceeds rapidly. However, little advantage is obtained by providing a large excess of dimethylamine reactant for greater equilibrium-shifting effect, and the addition rate of the cyclohexanone has little effect on the product distribution. Accordingly, the most preferred ratio of the reactants provides that only up to about 1.1 mols per mol cyclohexanone are added of the dimethylamine.

The use of an approximately stoichiometric ratio provides an added benefit, in that the products of the reaction in those instances where the ratio of dimethylamine to cyclohexanone is kept in the range of from about 1.0 to about 1.1 mols dimethylamine per mol cyclohexanone undergo a phase separation on being permitted to settle.

At high ratios, where greater amounts of dimethylamine are present, the product mixture is homogeneous. Separation of the product mixture at these higher ratios thus entails a fairly lengthy and efficient distillation, whereas the separation is facilitated over the most preferred range in that the greatest portion of the water produced by the reaction may simply be decanted or similarly removed.

It has been discovered also that Raney copper has much higher selectivity with regard to the hydrogenation of the amino-alcohol as compared to the cyclohexanone reactant than does the Raney nickel catalyst, such that the production of cyclohexanol is greatly reduced in comparison with the same reaction when conducted with the Raney nickel catalyst.

In addition, the Raney copper catalyst retains its activity in the presence of the product mixture when the reactor is shut down for extended periods of time, whereas the Raney nickel catalyst deactivates readily in the presence of the product mixture. Further, the Raney copper catalyst is advantageous in that it is not pyrophoric.

The general procedure for the most preferred embodiment of the process comprises charging a stirred tank-type reactor with the Raney copper under an inert atmosphere such as nitrogen or argon, followed by dimethylamine, which is added under a hydrogen atmosphere. The system is then pressurized with hydrogen and the cyclohexanone is pumped in at the reaction temperature, using a heat source such as steam to bring the vessel up to the reaction temperature prior to the addition of the cyclohexanone. After hydrogen consumption has ceased, and after any contemplated high temperature finish, the product mixture is permitted to cool and the catalyst to settle. The product mixture is pressured out and preferably distilled. Because of the lower boiling points of dimethylamine and cyclohexanone, unreacted cyclohexanone and dimethylamine may generally be present in the product fore-run which will either be recycled eventually or discarded.

The order of distillation will dictate that unreacted dimethylamine will distill out first, followed by a water/dimethylcyclohexylamine azeotrope which undergoes phase separation once taken overhead and from which water may be thus suitably removed, followed by unreacted cyclohexanone at a high reflux ratio, a cyclohexanol fraction at a high reflux ratio, and the object dimethylcyclohexylamine fraction. The cyclohexanone and cyclohexanol fractions will contain some dimethylcyclohexylamine, albeit with much smaller loss of the desired product than would occur in the Raney nickel catalyzed reaction, where greater amounts of cyclohexanol are produced. The dimethylamine and cyclohexanone fractions may be recycled as unreacted starting material to the reactor for further reaction.

The present invention is illustrated by the following examples.

PROCEDURE

The Raney copper catalyst was prepared using the W-2 Raney nickel procedure known to the art (Organic Syntheses, Coll. Vol. 3, Page 181, 1955) with the following modifications: the etching temperature was increased to 45° C. and the slurry was held at 45° C. until hydrogen evolution had stopped. The catalyst was then washed with deionized water until the pH was between 8 and 10. The alcohol washings were eliminated and the catalyst was stored under water.

The general reaction procedure for the examples was as follows. Raney copper catalyst, in the amount of 15 to 20 grams, was charged to a one gallon autoclave under a nitrogen blanket. The autoclave was closed, and purged with nitrogen followed by three pressure/vent hydrogen purge cycles. With full cooling, dimethylamine (DMA in Table I) in the amount of 10 to 12½ moles was transferred to the autoclave. Cooling water was then shut off and the autoclave was brought to the reaction temperature using low pressure steam. The system was then pressurized with hydrogen and cyclohexanone ($CyC_6=O$ in Table I) in the amount of 10 moles was pumped in. Addition times varied from 2-4 hours.

After hydrogen up-take had stopped (about 2-4 hours after the addition of the cyclohexanone), the reactant was cooled. The catalyst was allowed to settle, and the product was pressured out. A summary of the runs is found in Table I, wherein $CyC_6OH$ represents cyclohexanol and DMCHA signifies dimethylcyclohexylamine. The products were analyzed by gas chromotography using a 25 meter methylsilicone quartz capillary column and a flame ionization detector. The temperature program was 3 minutes at 55° C., 6° per minute to 110° C., then 1 minute at 110° C.

Fractionation of the runs was accomplished using a 25 millimeter by one meter packed column (with a hole size of 0.16 in. protruded metal packing) along with a 15 tray 25 millimeter Oldershaw column. A first charge was used to establish column hold-up and the kettle bottoms. A second charge of dry crude dimethylcyclohexylamine was then fractionated, the water having been removed previously by azeotropic distillation or by decanting. The yield of dimethylcyclohexylamine from this fractionation was 87 percent and the average of the two fractionations was 82 percent. Purity of the dimethylcyclohexylamine product was in excess of 99% after distillation. The column hold-up and kettle bottoms were significant losses for the first run. Results of the product fractionations from the two runs that were made are found in Table II, which employs the same symbols used in Table I.

In Table I, the formation of a two-phase product was not observed until the third run was completed. The second run, which also used an input ratio of 1 part by weight dimethylamine per part by weight cyclohexanone, was likely influenced by the presence of a remainder of the products of the first run, which employed a 1.25:1 ratio. Portions of preceding runs were left in the autoclave to avoid drawing off some of the settled catalyst.

TABLE I

DMCHA Synthesis Data

| Run No. | $DMA/CyC_6 = O$ Ratio | Acetic Acid | Temp., °C. | $H_2$ Press. | Addn. Time (hr.) | DMA | Crude DMCHA Analysis (Area %) | | |
|---|---|---|---|---|---|---|---|---|---|
| | | | | | | | $CyC_6 = O$ | $CyC_6OH$ | DMCHA |
| 1 | 1.25:1 | 1% | 130–147 | 300 | 2 | 5.0 | 0.41 | 2.4 | 92.2 |
| 2 | 1:1 | 1% | 112–115 | 300 | 2 | 1.7 | 1.0 | 2.0 | 95.3 |
| 3 | 1:1 | 1% | 102–106 | 205–315[1] | 2½ | 2.5 | 0.27 | 1.1 | 96.1[5] |
| 4 | 1.1:1 | 1% | 105–106 | 205 | 2 | 3.6 | 8.4 | 0.39 | 87.5 |
| 5 | 1.1:1 | 1% | 106–110[2] | 250 | 3⅜ | 5.6 | 9.5 | 0.32 | 84.3[3] |
| | | | | | | 2.6 | 1.8 | 0.8 | 94.8[4] |
| 6 | 1.25:1 | 1% | 112–115 | 300 | 4 | 5.6 | 4.4 | 0.63 | 89.5 |
| 7 | 1.1:1 | 4% | 114–117 | 250 | 2 | 2.0 | 0.44 | 0.41 | 97.2 |

[1]Hydrogenation finished at 325 psi $H_2$.
[2]Hydrogenation finished at 145° C., 300 psi $H_2$.
[3]Before high temperature finish.
[4]After high temperature finish.
[5]2-phase product.

TABLE II

DMCHA Fractionation Data

| Dried DMCHA Crude | Cut # | Temp., °C./ Barometric Pressure (mm Hg.) | Reflux Ratio | Wt. (g) | GC (Area %) | | | |
|---|---|---|---|---|---|---|---|---|
| | | | | | $C_4C_6=O$ | $C_4C_6OH$ | Unknown | DMCHA |
| Run #5 | 1 | 143–160/753 | 10:1 | 56.5 | 37 | 7 | 2 | 53 |
| | 2 | 160–165/753 | 10:1 | 57.6 | 2.1 | 9.3 | 0.8 | 87.2 |
| | 3 | 165/748 | 5:1 | 969.6 | nil | <0.1 | nil | 100 |
| | | | | DMCHA Yield 76% | | | | |
| | | Losses Due to Column Hold-Up and Kettle Bottoms | | | | | | |
| Run #7 (97% of theoretical DMCHA) | 1 | 99–160/752 | 20:1 | 47.3 | 16 | 8 | 2 | 74 |
| | 2 | 160–164/752 | 15:1 | 46.5 | 0.9 | 5 | 0.6 | 93.5 |
| | 3 | 164–165/744 | 3:1 | 1107.9 | nil | 0.2 | nil | 99.8 |
| | | | | DMCHA Yield 87% Material Balance 97% AVERAGE OF 2 RUNS 82% | | | | |

It can be seen from Tables I and II that the process the present invention produced the tertiary amine dimethylcyclohexylamine in 87 percent yield with a minimum of byproducts at a relatively low temperature and pressure, and with an efficient and effective separation of the products from each other and from the catalyst.

The present invention is thus well adapted to carry out the objects and attain the ends and advantages mentioned above as well as those inherent therein. While reasonable variations and modifications which will become apparent to those skilled in the art can be made, such changes and modifications are included within the spirit of this invention as defined by the appended claims.

What is claimed is:

1. A process for the preparation of dimethylcyclohexylamine, comprising reacting dimethylamine with cyclohexanone in the liquid phase in the presence of an unsupported Raney copper catalyst under hydrogenating conditions.

2. The process of claim 1 further comprising providing an acid as a condensation promoter.

3. The process of claim 2 wherein said acid is acetic acid and said acetic acid is present in a concentration in the range of from about 1 percent by weight to about 4 percent by weight of cyclohexanone added.

4. The process of claim 1 wherein said reaction is conducted under a partial pressure of hydrogen of at least 200 psig.

5. The process of claim 1 wherein said reaction is conducted under a pressure of hydrogen of about 250 psig.

6. The process of claim 1 wherein said reaction is conducted at a temperature in the range of from about 100° C. to about 120° C.

7. The process of claim 1 wherein said reaction is conducted at a temperature in the range of from about 115° C. to about 120° C.

8. The process of claim 1 wherein said dimethylamine is present in the range of from about 1 to about 1.25 mols of dimethylamine per mol cyclohexanone added.

9. The process of claim 1 wherein said dimethylamine is present at about 1.1 mols of dimethylamine per mol cyclohexanone added.

10. The process of claim 1 further comprising the steps of:
    permitting, over a period of time, gravitational separation of said Raney copper catalyst from liquid post-reaction material;
    removing said post-reaction material from contact with said catalyst; and
    separating said post-reaction material into fractions.

11. The process of claim 10 wherein said step of separating said post-reaction material into fractions includes distillation.

12. The process of claim 10 wherein said step of separating said post-reaction material into fractions comprises the steps of:
    first, distilling out an unreacted dimethylamine fraction;
    second, distilling out a water/dimethylcyclohexylamine azeotrope fraction and allowing gravitational separation of said azeotrope so that water is removed and dimethylcyclohexylamine contained in said zeotrope is recovered;
    third, distilling out an unreacted cyclohexanone fraction;
    fourth, distilling out a cyclohexanol fraction; and
    fifth, distilling out a dimethylcyclohexylamine fraction.

* * * * *